United States Patent
Gildenberg

(10) Patent No.: US 6,741,883 B2
(45) Date of Patent: May 25, 2004

(54) AUDIBLE FEEDBACK FROM POSITIONAL GUIDANCE SYSTEMS

(75) Inventor: Philip L. Gildenberg, Houston, TX (US)

(73) Assignee: Houston Stereotactic Concepts, Inc., Houston, TX (US)

(*) Notice: Subject to any disclaimer, the term of this patent is extended or adjusted under 35 U.S.C. 154(b) by 151 days.

(21) Appl. No.: 10/085,212

(22) Filed: Feb. 28, 2002

(65) Prior Publication Data

US 2003/0163040 A1 Aug. 28, 2003

(51) Int. Cl.$^7$ .................................................. A61B 5/05
(52) U.S. Cl. ........................ 600/429; 600/417; 600/424; 606/130
(58) Field of Search ................................ 600/407, 411, 600/414, 417, 425, 426, 427, 429, 437, 439, 424; 606/130; 378/20, 205

(56) References Cited

U.S. PATENT DOCUMENTS

| | | | |
|---|---|---|---|
| 5,423,832 A | | 6/1995 | Gildenberg |
| 5,662,111 A | * | 9/1997 | Cosman ....................... 600/417 |
| 5,855,582 A | | 1/1999 | Gildenberg |
| 5,871,445 A | * | 2/1999 | Bucholz ...................... 600/407 |
| 5,961,456 A | | 10/1999 | Gildenberg |
| 6,076,008 A | | 6/2000 | Bucholz |
| 6,083,163 A | | 7/2000 | Wegner et al. |
| 6,167,296 A | | 12/2000 | Shahidi |
| 6,175,756 B1 | | 1/2001 | Ferre et al. |
| 6,193,657 B1 | | 2/2001 | Drapkin |
| 6,283,763 B1 | | 9/2001 | Matsuzaki et al. |
| 6,285,902 B1 | * | 9/2001 | Kienzle et al. ............... 600/427 |
| 6,314,310 B1 | | 11/2001 | Ben-Haim et al. |

OTHER PUBLICATIONS

Gildenberg et al., "Chaper 23—Stereotactic Craniotomy with the Exoscope," Advanced Neurosurgical Navigation, 1999.
Galloway, "Chapter 21—Frameless Stereotactic Systems," Textbook of Stereotactic and Functional Neurosurgery, 1998.

* cited by examiner

*Primary Examiner*—Eleni Mantis Mercader
(74) *Attorney, Agent, or Firm*—Vinson & Elkins L.L.P.

(57) ABSTRACT

A computer-based system generating audible feedback to assist with guidance of at least one trackable point in space is provided. Surgical embodiments include generating audible feedback (to supplement visual and tactile feedback) to a surgeon moving the tip of a probe, for example, in a surgical field with respect to a volume of interest such as a tumor. Other surgical embodiments include generating audible feedback to assist with the precise insertion of a pedicle screw. In such surgical embodiments, as a surgeon moves a probe or instrument within the surgical field, a computer analyzes the current position of the probe and/or instrument in space with respect to a system of fiducial markers. The computer then provides audible feedback to the surgeon as to the position of the probe and/or instrument with respect to predetermined feature(s) of interest (such as a tumor) previously identified on a computer reconstruction of the surgical view obtained, for example, by a magnetic resonance imaging (MRI) scan, a computerized tomography (CT) scan and/or an ultrasound scan. The audible feedback may vary in numerous ways, such as in tone, volume, pattern and/or style, as the probe and/or instrument moves relative to the feature(s) of interest.

22 Claims, 2 Drawing Sheets

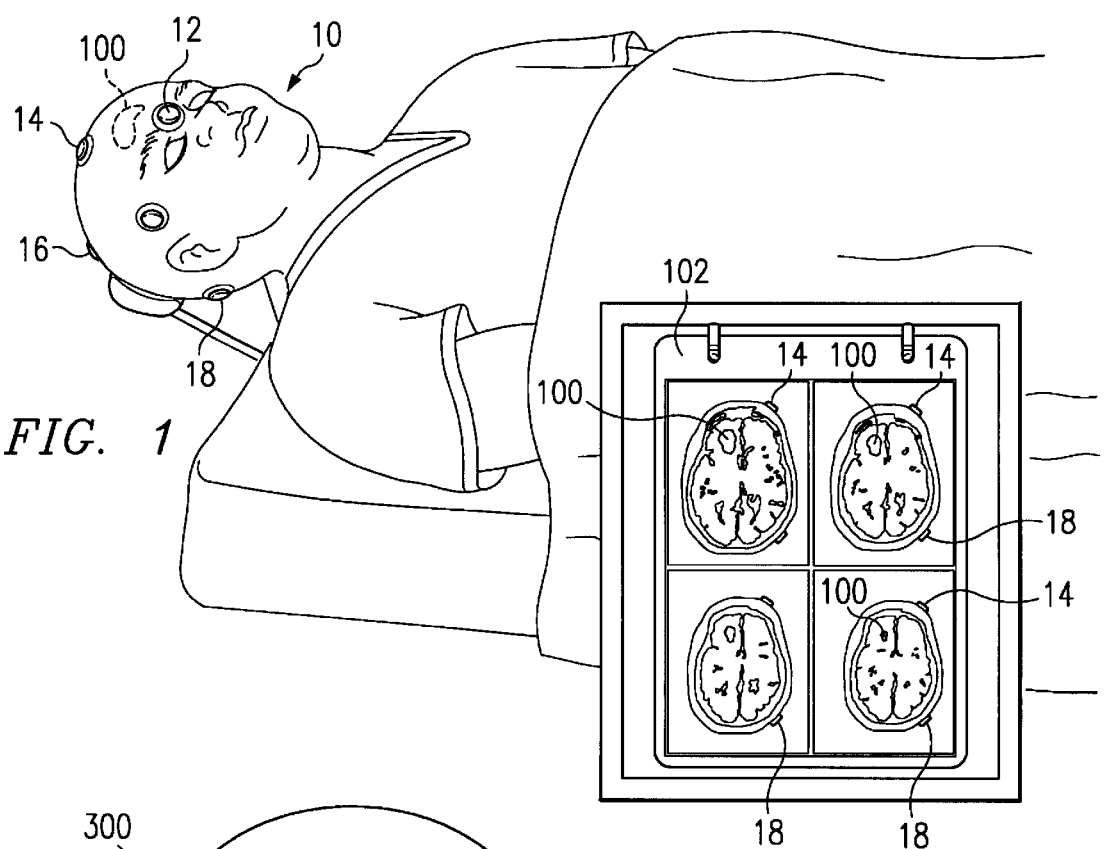
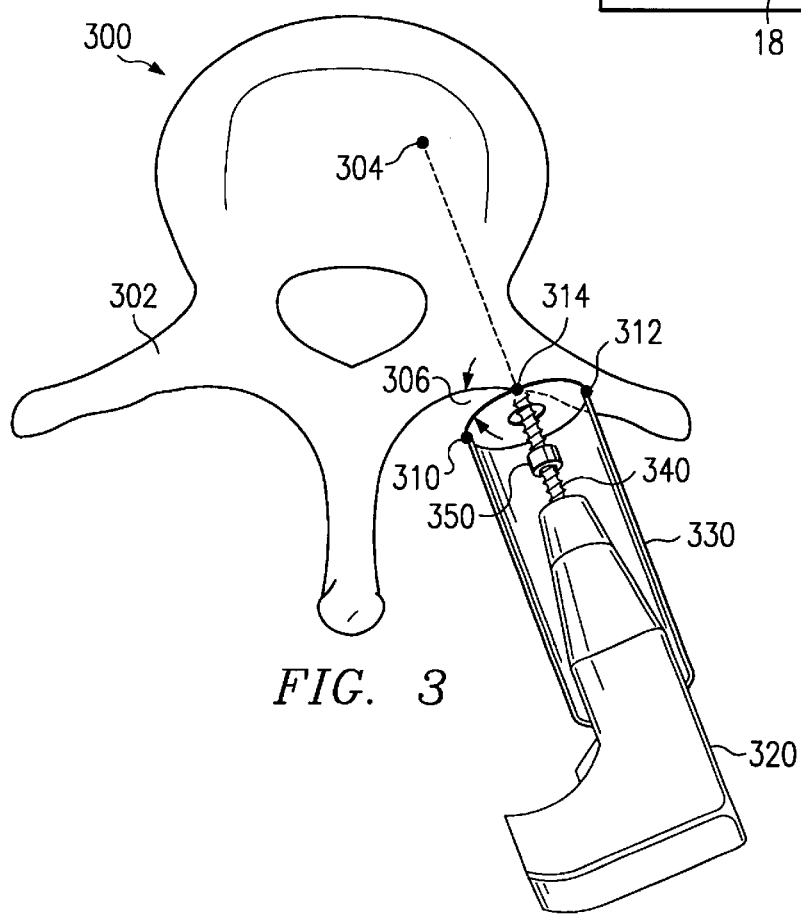

AUDIBLE FEEDBACK FROM POSITIONAL GUIDANCE SYSTEMS

TECHNICAL FIELD OF THE INVENTION

This application relates generally to audible feedback from 3-dimensional (3-D) imagery, and more specifically to embodiments in which a surgeon receives audible feedback based on the location of a surgical instrument as mapped on reconstructed surgical views.

BACKGROUND OF THE INVENTION

Stereotactic surgery is known in the art as a technique for localizing a target in surgical space. The use of stereotactic instrumentation based on tomographic imaging is conventional in surgery. When used for brain or other neurosurgery, such methods may involve attaching a headring apparatus to the patient's skull, and then using conventional techniques to acquire imaging data where the data is space-related to the headring. A surgeon may use an arc system to relate the position of the head to the radiographic image. An indexing device, localizer structure or other fiducial apparatus is generally used to specify quantitative coordinates of targets (such as tumors) within the patient's head relative to the fiducial apparatus. An exoscope may be used to aid in visualization during the procedure.

Current technology also allows use of a frameless system, to provide a visual reference in the operating room. Again with reference to brain surgery, fiducial markers are placed around the patient's head so as to be apparent on the pre-operative magnetic resonance imaging (MRI) or computerized tomography (CT) scan. Techniques known in the art are used pre-operatively to localize the fiducial markers located on the patient, and a computer compares this information to that from the previous imaging. The actual location of the patient's head may thus be registered to, and correlated with, the computerized three-dimensional reconstruction of the patient's head.

As the surgery proceeds the surgeon can use the image guidance system to locate the surgical target and track a resection instrument's position in space, relative to the target, based on the live-time recognition of fiducial markers located on the instrument itself. Such image guidance systems using visual feedback to the image are disclosed and discussed in more detail in U.S. Pat. No. 5,961,456, incorporated herein by reference. Embodiments disclosed in U.S. Pat. No. 5,961,456 allow the surgeon to observe a video monitor that projects an actual, real-time image of the surgical field and the instrument moving in space. Superimposed on that image is an augmented-reality image, derived from the pre-operative scan, disclosing the position of the target.

As the surgery proceeds, the surgeon can use the image guidance system to locate the surgical target. The same guidance system can localize in space the relation of the resection instrument to the target. While serviceable and useful for improved guidance for the surgeon, such prior art visual feedback systems require the surgeon periodically to re-orient his/her field of view from the surgical instrument and the patient to the monitor in order to track the instrument. Further advantages would be available if the surgeon were able to localize the target, and define its volume, while continuously viewing the surgical field.

A further variation on the above conventional technology is for the surgeon to perform frameless stereotactic surgery with the assistance of a microscope. The microscope assists enlarged viewing of the surgical field. In this application, the surgeon views a two-dimensional image from the pre-operative scan superimposed on a corresponding three dimensional volume within the surgical field seen directly through the microscope. Although helpful for fine and delicate surgical procedures on microscopic tumors, this technique has limited benefit since the field of view of the microscope is small and microscope programs may not be available at a particular institution. A system using pre-operative scans to guide the surgeon in both enlarged and unenlarged environments would be highly advantageous.

SUMMARY OF THE INVENTION

These and other needs in the art are addressed by a computer-based system generating audible feedback to assist with guidance of a trackable point in space. Surgical embodiments include generating audible feedback (to supplement visual and tactile feedback) to a surgeon moving the tip of a probe, for example, in a surgical field with respect to a volume of interest such as a tumor. Other surgical embodiments include generating audible feedback to assist with the precise insertion of a pedicle screw, inserting a biopsy cannula or electrode into the brain, and the like.

Exemplary surgical embodiments are based on correlating a three-dimensional (3-D) reconstruction of an anatomical object to real-time stereotactic surgery via a lexicon of audible signals. More specifically, these audible signals may be generated according to the position of the point of a probe or other instrument in surgical space, as seen by two or more cameras in relationship to a plurality of fiducial or fiduciary markers. The views of the cameras have previously been matched with a 3-D reconstruction of the surgical field or surgical target via the fiducial markers. Features of interest visible on the 3-D reconstruction, such as points, boundaries, planes and/or volumes, have previously been identified and correlated with predetermined audible feedback. As the surgeon moves a probe or instrument within the surgical field, a computer analyzes the current position of the probe or instrument in space with respect to the fiducial markers, and provides audible feedback as to its position relative to the predetermined features of interest identified on the 3-D reconstruction. The audible feedback may vary in numerous ways, including, but not limited to, changes in tone, volume, pattern and/or style, as the probe and/or instrument moves relative to the features of interest identified on the 3-D reconstruction.

Various illustrative embodiments of present invention provide a rich and comparatively unburdened sensory modality in the operating room and may be practiced independent of, or along with, conventional visually-oriented systems and techniques.

According to one aspect, therefore, a method for generating audible feedback is provided, the method comprising creating a computer-generated reconstruction of an overall volume, the reconstruction identifying one or more features of interest within the overall volume and creating a computer-generated real-time image of the overall volume, the computer-generated real-time image further including at least one trackable point, the trackable point(s) movable in real-time with respect to the overall volume. The method also comprises causing a computer to overlay the computer-generated real-time image and the computer-generated reconstruction with substantial spatial identity and substantial spatial fidelity, causing the computer to track the trackable point(s) with substantial positional fidelity to the real-time image, and creating computer-generated audible feedback, the feedback describing the position of the trackable point(s) with respect to the feature(s) of interest.

According to a second aspect, a method for generating audible feedback is provided, the method comprising creating a computer-generated 3-D reconstruction of an overall volume from a series of layered images, the reconstruction identifying one or more features of interest within the overall volume and creating a computer-generated real-time 3-D image of the overall volume by resolving digital output from at least two video cameras, the computer-generated real-time image further including at least one trackable point, the trackable point(s) movable in real-time with respect to the overall volume. The method also comprises causing a computer to overlay the computer-generated real-time image and the computer-generated reconstruction with substantial spatial identity and substantial spatial fidelity via reference to a system of fiducial markers, causing the computer to track the trackable point(s) with substantial positional fidelity to the real-time image, creating computer-generated audible feedback, the feedback describing the position of the trackable point(s) with respect to the feature (s) of interest, and selectably causing the audible feedback to vary in a predetermined fashion as a selected trackable point or points approach and/or withdraw from a predefined feature or features of interest.

According to a third aspect, a computer program product having computer-readable logic recorded thereon for generating audible feedback is provided, the computer program operable on a general purpose computer, the computer including a processor, a memory and a sound generator, the computer-readable logic comprising instructions for causing the computer to refer to a computer-generated reconstruction of an overall volume, the computer-generated reconstruction identifying one or more features of interest within the overall volume, and instructions for causing the computer to refer to a computer-generated real-time image of the overall volume, the computer-generated real-time image further including at least one trackable point, the trackable point(s) movable in real-time with respect to the overall volume. The computer-readable logic also comprises instructions for causing the computer, via reference to a system of fiducial markers, to overlay the computer-generated real-time image and the computer-generated reconstruction with substantial spatial identity and substantial spatial fidelity, instructions for causing the computer to track the trackable point(s) with substantial positional fidelity to the computer-generated real-time image, and instructions for causing the computer to generate audible feedback, the feedback describing the position of the trackable point(s) with respect to the feature (s) of interest.

It is, therefore, a technical advantage of various illustrative embodiments of the present invention that in surgical embodiments, audible sound may be used to provide positional feedback to a surgeon during a procedure. This allows the surgeon to receive positional feedback without the need for frequent reference to a monitor and/or a screen during surgery. Requiring the surgeon to look back and forth between a monitor and a surgical field will usually lengthen operating time. An increased risk of infection is often associated with increased operating time. In addition, the cost of a surgery diminishes with decreased operating time. Furthermore, using a monitor for orientation during the stereotactic procedure requires that a two-dimensional (2-D) monitor be related to a 3-D anatomical object. By using audio for guidance rather than solely video, the entire operation can be performed in a three-dimensional (3-D) environment.

A further technical advantage of various illustrative embodiments of the present invention is that, in surgical embodiments, increased precision during the operation is likely to result. This, in turn, is likely to result in a decreased possibility of neurological damage, scarring and/or adhesion formation.

A further technical advantage of various illustrative embodiments of the present invention is that the boundaries of an anatomical object such as a tumor may be discovered. Boundaries of anatomical objects such as tumors are often difficult to determine with a camera, magnification, and/or the naked eye. However, boundaries may be more accurately determined on a radiographic image. In surgical embodiments, various illustrative embodiments of the present invention enable audible feedback to be used to determine actual tissue boundaries with the help of a 3-D reconstructed image. As a result, the boundaries of an anatomical object may be more accurately determined. Other surgical embodiments provide audible feedback further correlated to the distances and orientation of the tip of the probe from the surgical feature(s) of interest.

A further technical advantage of various illustrative embodiments of the present invention is that the location of an anatomical object may be more easily and precisely determined. For example, various illustrative embodiments of the present invention may be useful for the insertion of pedicle screws, biopsy cannulas, electrodes and/or the like.

Although not discussed in detail, a similar coded audible signal can be used without the video display, for instance, on insertion of a biopsy needle or electrode with either a stereotactic frame or frameless guidance system. In addition, the audible signal can be used for other purposes besides surgery which may include engraving, carving, mounting, and/or inserting objects.

The foregoing has outlined rather broadly many of the features and technical advantages of the present invention in order that the detailed description of the present invention that follows may be better understood. Additional features and advantages of the present invention will be described hereinafter which form the subject of the claims of the present invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the present invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which the leftmost significant digit in the reference numerals denotes the first figure in which the respective reference numerals appear, and in which:

FIG. 1 schematically illustrates an embodiment in which a patient is being prepared for brain surgery assisted by audible feedback techniques;

FIG. 3 schematically illustrates a further embodiment in which audible feedback assists accurate insertion of a pedicle screw.

DETAILED DESCRIPTION OF THE INVENTION

Figure 2:
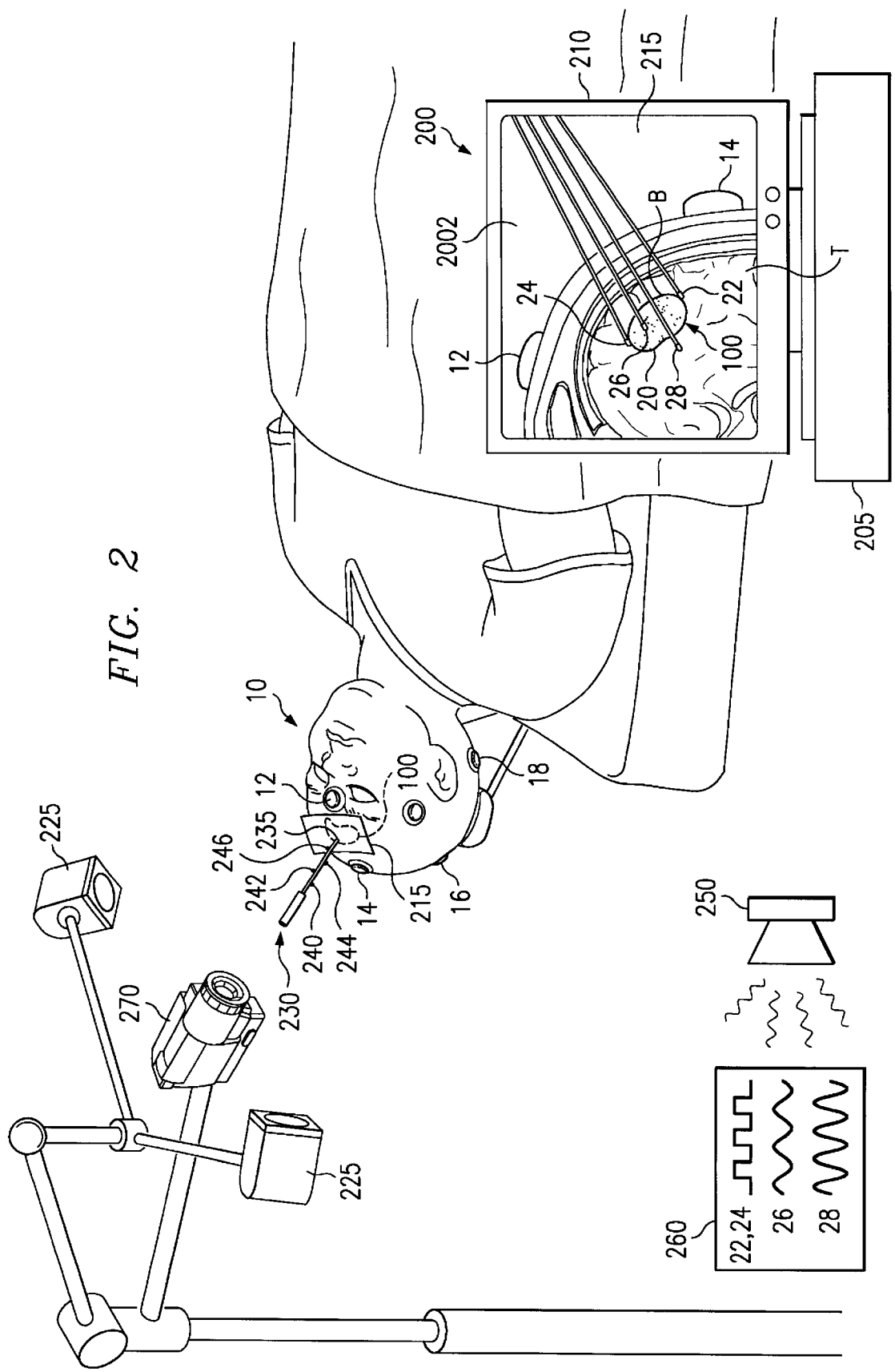
FIG. 2 schematically illustrates the patient depicted in FIG. 1 during surgery.

FIGS. 1 and 2 illustrate schematically an embodiment of the present invention in which brain surgery is assisted with audible feedback. It will be appreciated that the present invention is not limited to the brain surgery embodiments depicted in FIGS. 1 and 2. It will be further appreciated that embodiments are possible in any application in which it is advantageous to use audible signals to monitor and/or guide, substantially in real-time, the location of a probe and/or other workpoint in relation to a field of work.

FIG. 1 schematically illustrates a supine patient's head 10 with a brain tumor 100. The patient is prepared for a stereotactic surgical procedure to use audible feedback as disclosed in this application. Surrounding the patient's head are fiducial markers 12, 14, 16 and 18. It will be understood that numerous fiducial marker systems are known in the art and that the number of fiducial markers used may vary as appropriate. Some systems attach the fiducial markers directly to the patient's head, an example of which is illustrated in FIG. 1. Other systems, examples of which are not illustrated, may use frame-based stereotactic systems which are well-defined in the prior art. It will be understood that the present invention is not limited to any particular type of fiducial marker system.

With further reference to FIG. 1, a series of layered images 102 depict the patient's head/brain 10 and the tumor 100 at various points of section. The layered images 102 were previously obtained and computer-recorded during a pre-operative procedure using well-known techniques such as magnetic resonance imaging (MRI) and/or computerized tomography (CT) and/or ultrasound, and the like. FIG. 1 further depicts the layered images 102 including the fiducial markers 12, 14, 16 and 18 recorded on the images, and aligned with the patient's head 10 during imaging in the same aspect as for the stereotactic procedure.

FIG. 1 schematically illustrates the tumor 100 as the item or feature of interest in this embodiment. It will be appreciated that the present invention is not limited in this regard. The item of interest may be any point, object, volume and/or boundary in three-dimensional space in reference to which audible feedback would be advantageous to help guide probes and/or other instruments in the space. It will be appreciated that brain tumor surgery is one useful application of the technology, since audible feedback may help guide the surgeon's hands in the delicate surgical field of brain tissue, although the technique may be applied to other surgical and/or non-surgical fields, as well. For instance, some examples where this technology would be advantageous include alternative positional guidance systems without images, non-imaging anatomical guidance systems, and research applications.

FIG. 2 schematically illustrates the patient of FIG. 1 undergoing surgery using audible feedback. Computer system 200 includes a processor 205 and a monitor 210. It will be understood that the computer system 200 may generate and display a reconstructed 3-D image of the patient's head and brain according to 3-D resolution of the series of layered images 102 acquired earlier and described above with reference to FIG. 1. The monitor 210 is shown on FIG. 2 displaying a view 215 comprising an enlarged 3-D zone of such a computer-generated reconstructed 3-D image. It will be seen on FIG. 2 that the view 215 displayed on the monitor 210 is only a partial view of the patient's head/brain 10, wherein a surgical field including the tumor 100 is visible. Computerized techniques well-known in the art will be able to enlarge or reduce the magnification of the reconstruction of the layered images 102 and display same on the monitor 210.

It will be appreciated that the present invention is not limited to any particular computer system 200. Computer systems are known in the art, both stand-alone or networked, having the processing functionality to generate reconstructive 3-D images resolved from a series of layered views, and then to enlarge, rotate and/or generally manipulate the reconstructive image on a display. Examples of a suitable computer system 200 in current use include systems produced by Radionics/RSI of Burlington, Mass., or the Stealth Image Guided System produced by the Surgical Navigation Technology Division of Medtronic in Broomfield, Colo.

Alternatively (not illustrated), computer graphics images, based on imaging data, may be placed in the direct view field of a surgical microscope. For example, see U.S. Pat. No. 4,722,056 granted Jan. 26, 1988 to Roberts et al. Stealth Image Guided System produced by the Surgical Navigation Technology Division of Medtronic in Broomfield, Colo. also makes a system whose capability includes importing a reconstructed graphics image into a "heads-up" display seen concurrently with the surgical field, either directly or through a surgical microscope.

With further reference to FIG. 2, the fiducial markers 12 and 14 are visible on the view 215 displayed on the monitor 210. It will be understood that the overall reconstructive 3-D image generated to be displayed on the monitor 210 includes the fiducial markers 12, 14, 16 and 18 as captured from the series of layered images 102 described above with reference to FIG. 1.

Looking at the view 215 on the monitor 210 in FIG. 2 more closely, it will be understood that prior to surgery, the computer system 200 will have been coded to define and/or identify zones of interest visible in the reconstructive 3-D image. These zones of interest may include points, volumes, planes and/or boundaries visible on the reconstructive 3-D image and differentiable (able to be differentiated and/or distinguished) by the computer system 200. In the case of the example shown on FIG. 2, the computer system 200 has been previously coded to define and identify at least two volumes and one 3-D boundary: the tumor 100, healthy brain tissue T, and a boundary B between the tumor 100 and the healthy brain tissue T.

FIG. 2 also shows cameras 225 placed about the patient's head 10 to localize the fiducial markers 240, 242, 244 and 246 located on the surgical instrument 230 from different aspects. Camera 270 is placed to visualize the surgical field. Digital output signals from the cameras 225 and 270 are received by the computer system 200 (connections omitted for simplicity and clarity). The computer system 200 then resolves, using conventional computer processing techniques known in the art, the cameras' signals into a computer-generated combined "stereo" 3-D view of the patient's head 10.

Although FIG. 2 shows only one visualizing camera 270 and two localizing cameras 225 for simplicity and clarity, it will be appreciated that multiple additional cameras may be included. As is well understood in the art, the greater the number of cameras that are provided viewing the patient's head 10, the more sophisticated and detailed a "stereo" 3-D view of the head 10 may be obtained by concurrently resolving such multiple cameras' views.

With further reference to FIG. 2, a probe 230 is provided to the surgeon for use in the brain tissue of patient's head 10. The probe 230 provides a tip 235 on the end making contact with the tissue and provides a mechanism making it trackable by cameras 225. Typically the trackable mechanism may be the fiducial markers 240, 242, 244 and 246 mounted on the surgical instrument itself, which indirectly indicate the localization of the tip 235, although the present invention is not limited in this regard. Again, the number of fiducial markers used may vary as appropriate. The mechanism may comprise any type of source disposing the tip 235 to be trackable, including various forms of electromagnetic radiation and/or radioactive emissions, and the like.

As will be seen in FIG. 2, the cameras 225 track the fiducial markers 240, 242, 244 and 246 on the probe 230, and allow the locus of the tip 235 to be determined by the computer system 200. Thus, the computer-generated stereo 3-D view of the patient's head 10 based on the combined views of the cameras 225, with the 3-D view based in part on the pre-operative CT and/or MRI, and with the localization based on the combined views of the cameras, will further include the locus of the tip 235, as well as the fiducial markers 12, 14, 16, and 18.

It will be appreciated that the present invention is not limited to any type of instrument used by the surgeon in generating a trackable tip 235. Although the embodiment of FIG. 2 depicts the probe 230, the instrument used by the surgeon may be any suitable instrument upon which a trackable point or points may be deployed, such as a scalpel or other instrument. Indeed, it will be further appreciated that the present invention is not limited to use of a surgical instrument, or location of a trackable point on a tip, or confinement to one instrument and/or trackable point. Depending on the application and the deployment of the present invention, any number of instruments and/or trackable points may be used. Further, the trackable points may be deployed at any desired positions with respect to the instruments. Moreover, in embodiments where multiple trackable points are used, as long as different trackable points are disposed to exhibit different tracking signatures that are differentiable by the cameras 225, it will be appreciated that the computer-generated stereo 3-D view of the patient's head 10 based on the combined views of the cameras 225 may also include a separate locus for each of such different trackable points.

Returning to FIG. 2, the computer system 200 now overlays the computer-generated stereo 3-D view of the patient's head 10 (based on the combined views of the cameras 270 and 225), with the computer-generated reconstructed 3-D image of the patient's head and brain according to 3-D resolution of the series of layered images 102 (based on the pre-operative scan described above with reference to FIG. 1). Computer system 200 advantageously uses the fiducial markers 12, 14, 16 and 18 to coordinate and match the overlay of the computer-generated stereo 3-D view and the computer-generated reconstructed 3-D image view.

Once the computer-generated stereo 3-D view and the computer-generated reconstructed 3-D image view are coordinated, the computer system 200 may then relate the locus of the tip 235 of the probe 230, as tracked by the cameras 225, to the previously-coded zones of interest on the reconstructed 3-D image. Specifically, in the example depicted in FIG. 2, the computer system 200 will be able to use fiducial markers 12, 14, 16 and 18 and the fiducial markers 240, 242, 244 and 246 to triangulate the tip 235, as tracked by the cameras 225, and then pinpoint the current position of the tip 235 with respect to the previously-coded zone or zones of interest on the computer-generated reconstructed 3-D image. Thus, the computer system 200 will be able to identify when the tip 235 is in the tumor 100, or the healthy tissue T, or at the boundary B by reference to those previously-defined and previously-coded zone or zones of interest.

With further reference to FIG. 2, a loudspeaker 250 is provided to enable the computer system 200 to give an audible feedback 260 to the surgeon according to the position of the tip 235 with respect to the previously-coded zone or zones of interest on the reconstructed 3-D image. In the example depicted in FIG. 2, it will be seen that when the tip 235 is at positions 22 and 24, as shown on the monitor 215, the computer system 200 detects the tip 235 to be at the boundary B, and generates an audible feedback 260 comprising a buzz sound typical of a square wave, as indicated in FIG. 2 by the square wave shown in the audible feedback 260 associated with position numbers 22 and 24. When the tip 235 is at position 26, the computer system 200 detects the tip 235 to be in the tumor 100, and generates an audible feedback 260 comprising a pure tone typical of a sine wave, as indicated in FIG. 2 by the lower frequency, lower amplitude sine wave shown in the audible feedback 260 associated with position number 26. When the tip 235 is at position 28, the computer system 200 detects the tip 235 to be in the healthy brain tissue T, and generates an audible feedback 260 comprising a different (higher) tone, as indicated in FIG. 2 by the higher frequency, higher amplitude sine wave shown in the audible feedback 260 associated with position number 28.

Thus, the surgeon may receive audible feedback as to the position of an instrument with respect to a volume and/or boundary of interest within an overall surgical field. The surgeon may then use this audible feedback to augment the visual and/or tactile feedback received while performing the operation.

It will be appreciated that the present invention is not limited to the types of audible feedback described in exemplary form above with respect to FIG. 2. Consistent with the overall scope of the present invention, different audible feedbacks may vary in tone, volume, pattern, pulse, tune and/or style, for example, and may even include white noise, and/or pre-recorded utterances recognizable by the surgeon. In other embodiments, the audible feedback may be substituted for, and/or supplemented with, a complementary tactile feedback system comprising a vibrating device (not illustrated) placed where the surgeon may conveniently feel the vibration. Different audible feedbacks may be deployed to correspond to different types of vibratory feedback, including fast or slow, soft or hard, continuous or pulsed, increasing or decreasing, and so on. In various illustrative embodiments, for example, a steady tone could indicate that the zone of interest is being approached, with the pitch increasing until the border of the zone is reached by the dissection instrument and/or pointer, so the highest pitch would indicate contact with the zone or zones of interest. Furthermore, when the tip of the instrument lies within the zone or zones of interest, an interrupted tone at that highest target pitch could be heard, with the frequency of the signal increasing until becoming a steady tone when the border is reached.

It will be further appreciated that the present invention is not limited to embodiments where the audible feedback is static depending on the position of a trackable point with respect to predefined zones of interest. Dynamic embodiments (not illustrated) fall within the scope of the present invention in which, for example, the audible feedback may change in predetermined and recognizable fashions as the trackable point moves within a predefined zone of interest towards or away from another zone of interest. For example, if the audible feedback 260 on FIG. 2 comprises silence for all positions on the boundary B (including the positions 22 and 24), a pure sine wave tone for all positions in the tumor 100 (including the position 26) and a square wave "buzz" for all positions in the healthy brain tissue T (including the position 28), according to an exemplary dynamic embodiment (not illustrated), the computer 200 might be disposed to increase the pitch of the sine wave tone and the square wave "buzz" as the position of the tip 235 moved closer to the boundary B. Thus, the surgeon would be able to interpret the dynamic audible feedback in a yet further enhanced mode, in which both pitch and type of sound could be used adaptively to assist movement and/or placement of an instrument in the surgical field. Another illustrative system embodiment might involve intermittent pulsatile and/or pulsating sounds when the tip 235 lies within the tumor 10, with the rate of pulsation increasing as the boundary B is approached so the pulsation rate becomes substantially continuous at the boundary B and then silent outside the defined volume.

Of course, other dynamic variations on audible feedback are possible, such as changes in volume, and/or changes in predetermined utterances. These other variations may be substituted for the changes in pitch and/or type suggested above, and/or may supplement the same, to enhance yet further the audible feedback by making the audible feedback more multi-dimensional.

FIG. 3 shows a further illustrative embodiment of the present invention in an orthopedic application. As is known in conventional surgery, a screw (not shown) may be inserted into a pedicle 302 of a vertebra 300. Successful pedicle screw insertion relies in part on the surgeon knowing and achieving optimal depth of penetration and location of the screw, which depends on obtaining an optimal angle 306 of penetration. The dynamic audible feedback described above will be seen, in particular, to be useful in assisting insertion of a screw into the pedicle 302.

In FIG. 3, a drill 320 is used for insertion of a pilot hole into a pedicle 302. The angle of entry 306 of a drill bit 340 into the pedicle 302 predetermines the ability of the tip of the screw, which is inserted into the pilot hole, to achieve correct placement 304. A bit guard 350 is placed on the drill bit 340 before the drilling of the hole to obtain a desired distance for screw insertion. Located at one end of a drill guide 330 are three fiducial makers 310, 312, 314, which can be tracked by localizing cameras similar to those shown in FIG. 2. The data collected from the localizing cameras may be analyzed by one or more computers and an audible output will assist the surgeon in obtaining the correct angle 306 and location for insertion of the drill bit 340 to reach the target 304.

Those of skill in the art will also appreciate that the computerized aspects of the present invention may be embodied on software operable on a conventional computer system, such as those commercially-available computer systems described above, or, alternatively, on general purpose computers standard in the art having at least a processor, a memory and a sound generator. IBM, Dell, Compaq, Sun and other well-known computer manufacturers make general purpose processors for running software devised to accomplish the computerized functionality described herein with respect to the present invention. Conventional software languages such as UNIX and C++, well-known to be operable on such general purpose machines, may be used to create the software.

Although the present invention and its advantages have been described in detail, it should be understood that various changes, substitutions and alterations can be made herein without departing from the spirit and scope of the present invention as defined by the appended claims.

I claim:

1. A method for generating audible feedback, the method comprising:

(a) creating a computer-generated reconstruction of an overall volume, the computer-generated reconstruction identifying at least one feature of interest within the overall volume;

(b) creating a computer-generated real-time image of the overall volume, the computer-generated real-time image further including at least one trackable point, the at least one trackable point movable in real-time with respect to the overall volume;

(c) causing a computer to overlay the computer-generated real-time image and the computer-generated reconstruction with substantial spatial identity and substantial spatial fidelity;

(d) causing the computer to track the at least one trackable point with substantial positional fidelity to the computer-generated real-time image; and (e) creating computer-generated audible feedback, the computer-generated audible feedback describing movement of the at least one trackable point with respect to the at least one feature of interest.

2. The method of claim 1, wherein the computer-generated reconstruction and the computer-generated real-time image are both three-dimensional.

3. The method of claim 2, wherein creating the computer-generated real-time image of the overall volume further comprises localizing a head in part by resolving digital output from at least one video camera.

4. The method of claim 2, wherein the computer-generated reconstruction is generated in part by resolving a series of layered images.

5. The method of claim 3, wherein the series of layered images is obtained using a process selected from the group of:

(1) computerized tomography (CT);
(2) magnetic resonance imaging (MRI); and,
(3) ultrasound.

6. The method of claim 1, wherein the computer-generated audible feedback comprises at least one type of sound selected from the group consisting of:

(1) a tone;
(2) a buzz;
(3) a tune;
(4) white noise;
(5) a pre-recorded utterance;
(6) substantial silence; and
(7) an intermittent pulsatile tone.

7. The method of claim 1, wherein the computer-generated audible feedback comprises at least one variation selected from the group consisting of:

(1) pitch variation;
(2) volume variation;
(3) pulse variation;
(4) type of sound variation; and
(5) utterance variation.

8. The method of claim 1, wherein (c) and (d) are performed using a system of fiducial markers.

9. The method of claim 1, wherein the at least one trackable point is a tip of a surgical instrument.

10. The method of claim 1, wherein the overall volume includes at least a portion of animal tissue, and wherein the at least one feature of interest includes a tumor.

11. The method of claim 1, wherein the overall volume includes at least a portion of animal bone, and wherein the at least one feature of interest includes a predetermined insertion locus within the animal bone for an orthopedic device.

12. The method of claim 11, wherein the animal bone is a vertebra and the orthopedic device is a pedicle screw.

13. The method of claim 1, wherein the computer-generated audible feedback is generated to assist with the use of a surgical microscope.

14. The method of claim 1, further comprising:
(f) selectably causing the computer-generated audible feedback to vary in a predetermined fashion as a selected trackable point approaches and withdraws from a predefined feature of interest.

15. A method for generating audible feedback, the method comprising:
(a) creating a computer-generated 3-D reconstruction of an overall volume from a series of layered images, the computer-generated reconstruction identifying at least one feature of interest within the overall volume;
(b) creating a computer-generated real-time 3-D image of the overall volume by resolving digital output from at least two video cameras, the computer-generated real-time 3-D image further including at least one trackable point, the at least one trackable point movable in real-time with respect to the overall volume;
(c) causing a computer to overlay the computer-generated real-time 3-D image and the computer-generated 3-D reconstruction with substantial spatial identity and substantial spatial fidelity via reference to a system of fiducial markers;
(d) causing the computer to track the at least one trackable point with substantial positional fidelity to the computer-generated real-time 3-D image;
(e) creating a computer-generated audible feedback, the computer-generated audible feedback describing movement of the at least one trackable point with respect to the at least one feature of interest; and
(f) selectably causing the computer-generated audible feedback to vary in a predetermined fashion as at least one selected trackable point approaches and withdraws from a predefined feature of interest.

16. The method of claim 15, wherein the at least one trackable point is a tip of a surgical instrument.

17. The method of claim 15, wherein the overall volume includes at least a portion of animal tissue, and wherein the at least one feature of interest includes a tumor.

18. The method of claim 15, wherein the overall volume includes at least a portion of animal vertebra, and wherein the at least one feature of interest includes a predetermined insertion locus within the vertebra for a pedicle screw.

19. A computer program product having a computer-readable logic recorded thereon for generating an audible feedback, the computer program operable on a general purpose computer, the computer including a processor, a memory and a sound generator, the computer-readable logic comprising:
instructions for causing the computer to refer to a computer-generated reconstruction of an overall volume, the computer-generated reconstruction identifying at least one feature of interest within the overall volume;
instructions for causing the computer to refer to a computer-generated real-time image of the overall volume, the computer-generated real-time image further including at least one trackable point, the at least one trackable point movable in real-time with respect to the overall volume;
instructions for causing the computer, via reference to a system of fiducial markers, to overlay the computer-generated real-time image and the computer-generated reconstruction with substantial spatial identity and substantial spatial fidelity;
instructions for causing the computer to track the at least one trackable point with substantial positional fidelity to the computer-generated real-time image; and
instructions for causing the computer to generate audible feedback, the computer-generated audible feedback describing movement of the at least one trackable point with respect to the at least one feature of interest.

20. The computer program product of claim 19, wherein the computer-readable logic further comprises:
instructions for selectably causing the computer to vary the computer-generated audible feedback in a predetermined fashion as at least one selected trackable point approaches and withdraws from a predefined feature of interest.

21. The computer program product of claim 19, wherein the computer-readable logic further comprises:
instructions for causing the computer to generate the computer-generated reconstruction from a series of layered images.

22. The computer program product of claim 19, wherein the computer-readable logic further comprises:
instructions for causing the computer to generate the computer-generated real-time image by resolving digital output from at least two video cameras.

* * * * *